US006295649B1

(12) United States Patent
Kang

(10) Patent No.: US 6,295,649 B1
(45) Date of Patent: Oct. 2, 2001

(54) HEADGEAR FOR ADVERTISEMENTS, PUBLIC RELATIONS AND CHEERING AS WELL AS SHADING

(76) Inventor: Bong Ju Kang, 604-1002, Shindo Apartment, Howon-dong, Uijongbu-shi, Kyungki-do (KR)

( * ) Notice: Subject to any disclaimer, the term of this patent is extended or adjusted under 35 U.S.C. 154(b) by 0 days.

(21) Appl. No.: 09/524,428

(22) Filed: Mar. 13, 2000

(30) Foreign Application Priority Data

Nov. 17, 1999 (KR) ..... 99-50978

(51) Int. Cl.[7] ..... A61F 9/00

(52) U.S. Cl. ..... 2/12; 2/171; 2/200.3; 40/329

(58) Field of Search ..... 2/12, 171, 171.01, 2/171.03, 175.1, 184.5, 209.11, 200.3, 209.13; 40/329, 586

(56) References Cited

U.S. PATENT DOCUMENTS 1,030,173 * 1/1912 Haggerty ..... 2/171
2,153,146 * 4/1939 Holmes ..... 2/171
2,248,497 * 7/1941 Gelvin ..... 2/171
2,594,906 * 4/1952 Gardner ..... 2/171
2,880,423 * 4/1959 O'Reilly ..... 2/171
4,246,659 * 1/1981 Lyons ..... 2/175
5,406,645 * 4/1995 Lin ..... 2/10
6,081,922 * 7/2000 Wright ..... 2/12

* cited by examiner

*Primary Examiner*—John J. Calvert
*Assistant Examiner*—Katherine Moran
(74) *Attorney, Agent, or Firm*—Darby & Darby

(57) ABSTRACT

Headgear for advertisements, public relations and cheering as well as shading is disclosed. A head insertion hole and a sign part are defined on the center portion of a plate by a circumferential cut line and a front folding line. A plurality of linear cut lines, which are extended radially outwardly from the circumferential cut line, are formed on the portion of the plate outside of the sign part while being spaced apart from each other, thereby forming head holding portions between every two linear cut lines. In another embodiment, auxiliary traverse cut lines are formed to pass through the ends of the alternate linear cut lines, respectively, so that a resilient action of the head holding is easily performed. In a further embodiment, the headgear further comprises a restriction means that is attached to said sign part and the remaining portion of the plate, with a first end of the restriction means being fixed to the bottom surface of the sign part and a second end of the restriction means being fixed to the bottom surface of the remaining portion of the plate, so as to prevent the sigh part from being bent over excessively.

5 Claims, 3 Drawing Sheets

HEADGEAR FOR ADVERTISEMENTS, PUBLIC RELATIONS AND CHEERING AS WELL AS SHADING

BACKGROUND OF THE INVENTION

1. Field of the Invention

The present invention relates, in general, to headgear and, more particularly, to headgear for advertisements, public relations and cheering as well as shading, which not only obstructs the rays of the sun and serves as a display when the sign part stands erect, but also is used as a cheering card and a publicity plate when the sign part is not erected.

2. Description of the Prior Art

As well known to those skilled in the art, a broad-brimmed cap, which is used out of doors, serves to prevent a user's hair and scalp from being damaged by direct rays of the sun and protect a user's skin from being injured by ultraviolet rays of the sun. The cap may be made of various materials such as fabric or synthetic resin and may have various shapes.

Generally, event participants or sports game spectators may wear various broad-brimmed caps that they bring to the event or the sports game themselves and some of the participants or spectators use towels or newspapers so as to protect their faces from being damaged by the sunshine. As a result of the lack of conformity in the shape and style of such caps, there is also a lack of unity among the participants or spectators.

In order to overcome such a problem, uniform broad-brimmed caps made of paper may be provided by a host or sponsor of such an event or sports game to those participants or spectators. Since such caps are used mainly to obstruct the sunshine, advertisements and public relations effects are not sufficient in comparison with a manufacturing cost. Therefore, the host of the event or sports game hesitates to manufacture and provide such caps. In addition, the caps are easily removed undesirably from the head by wind or external force while out of doors. Further, when cheering is necessary, the participants or spectators should carry caps and cheering instruments with them, thereby rendering them to be troublesome. After cheering instruments are used in cheering, they are discarded, thereby cluttering up the surroundings and generating waste.

SUMMARY OF THE INVENTION

Accordingly, the present invention has been made keeping in mind the above problems occurring in the prior art, and an object of the present invention is to provide headgear for advertisements, public relations and cheering as well as shading, which not only obstructs the sunshine effectively, but also is used for advertisements, public relations and cheering.

In order to accomplish the above object, the present invention provides headgear for advertisements, public relations and cheering as well as shading, wherein a head insertion hole and a sign part are defined on the center portion of a plate by a circumferential cut line and a front folding line, and a plurality of linear cut lines, which are extended radially outwardly from the circumferential cut line, are formed on the portion of the plate outside of the sign part while being spaced apart from each other, thereby forming head holding portions between every two linear cut lines.

In another embodiment, auxiliary traverse cut lines are formed to pass through the ends of the alternate linear cut lines, respectively, so that a resilient action of the head holding is easily performed.

In a further embodiment, the headgear further comprises a restriction means that is attached to said sign part and the remaining portion of the plate, with a first end of the restriction means being fixed to the bottom surface of the sign part and a second end of the restriction means being fixed to the bottom surface of the remaining portion of the plate, so as to prevent the sign part from being bent over excessively.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
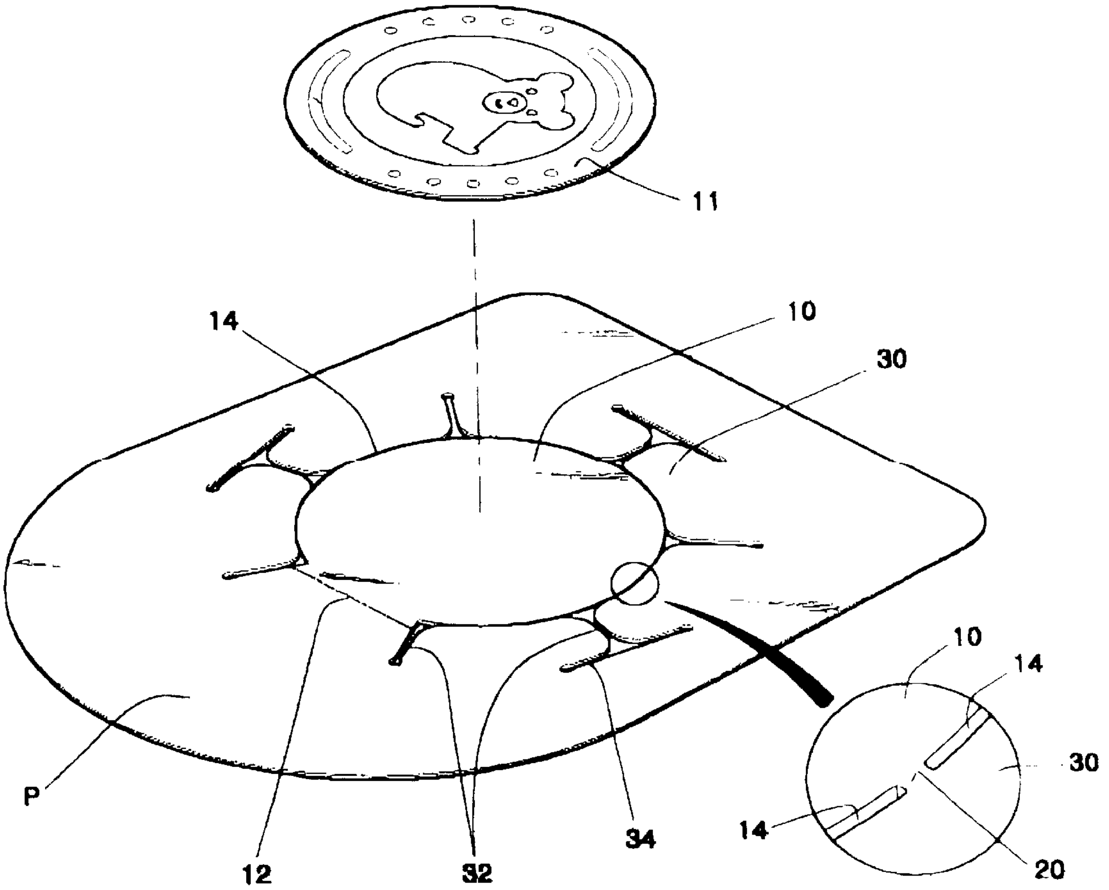
FIG. 1 is a perspective view showing headgear for advertisements, public relations and cheering as well as shading according to an embodiment of the present invention.
Figure 2:
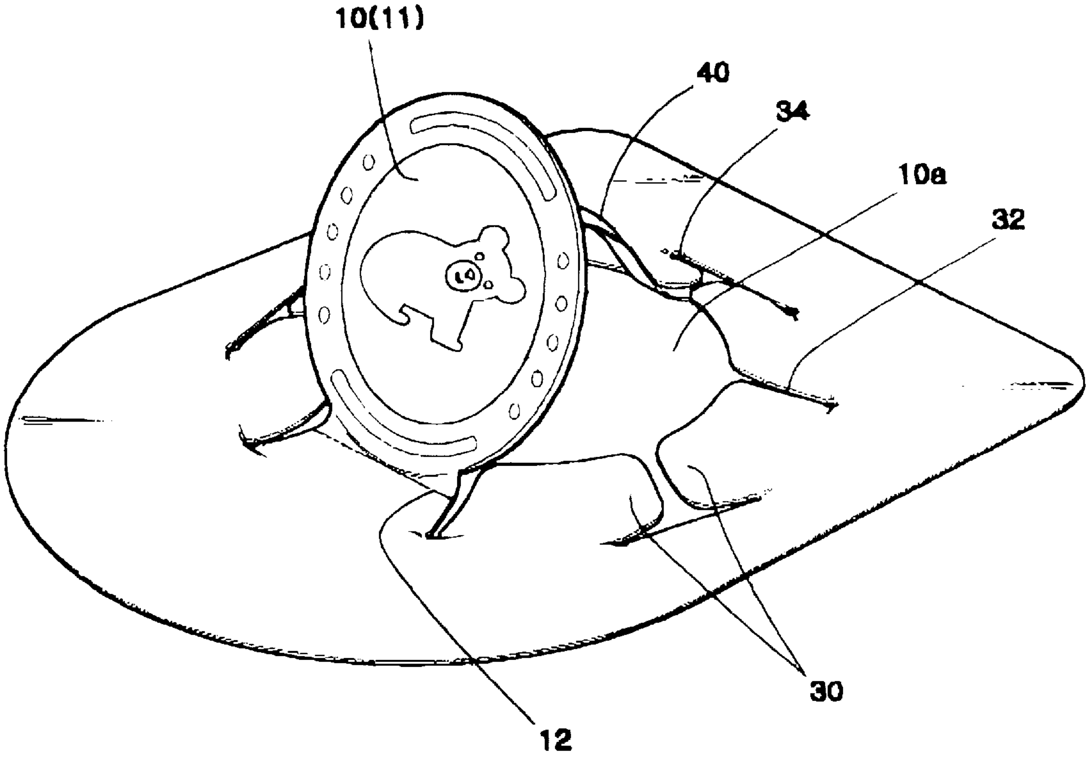
FIG. 2 is a perspective view showing the extended headgear of FIG. 1.
Figure 3:
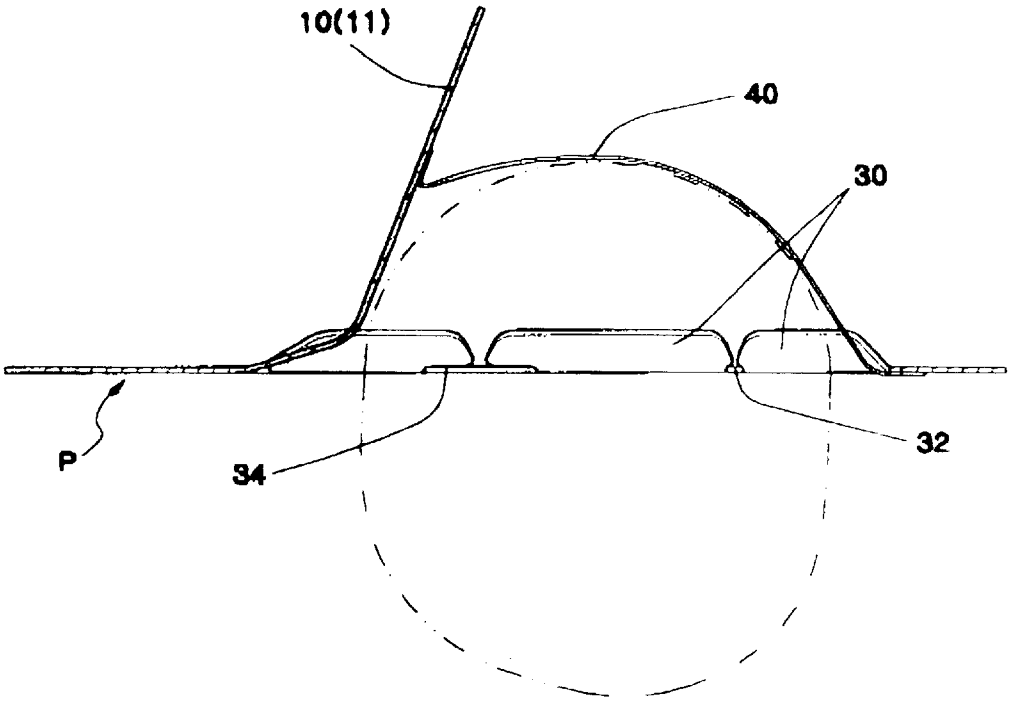
FIG. 3 is an elevational cross section of FIG. 2.

FIG. 1 is a perspective view showing headgear for advertisements, public relations and cheering as well as shading according to an embodiment of the present invention. FIG. 2 is a perspective view showing the extended headgear of FIG. 1. FIG. 3 is an elevational cross section of FIG. 2.

As shown in the drawings, the headgear of the present invention consists of a plate P. A head insertion hole 10*a* and a sign part 10 are defined on the center portion of the plate P by a circumferential cut line 14 and a front folding line 12, so that the sign part 10 stands erect when the head is inserted into the head insertion hole 10*a*.

Items that a headgear wearer would like to display may appear directly on the sign part 10, or a separate sheet 11 on which the items appear may be attached to the sign part 10.

A plurality of linear cut lines 32, which are extended radially outwardly from the circumferential cut line 14, are formed on the portion of the plate P outside of the sign part 10 while being spaced apart from each other, thereby forming head holding portions 30 between every two linear cut lines 32. Since the head holding portions 30 are positioned outside of the head insertion hole 10a, the head holding portions 30 are raised and resiliently press against the head when the head is inserted into the head insertion hole 10*a*.

Additionally, auxiliary traverse cut lines 34 may be preferably formed to respectively pass through the ends of the alternate linear cut lines 32 except the linear cut lines 32 that meet the folding lines 12. Since the fixed sides of the head holding portions 30 become narrower accordingly as the auxiliary traverse cut lines 34 are formed, the resilient action of the head holding portions 30 may be easily performed.

Each of the linear cut lines 32 and the auxiliary traverse cut lines 34 has no width, but may be replaced with a cut gap having a certain width so as to prevent interference with adjacent portions, as shown in the drawings. In order to prevent interference furthermore, the head holding portions 30 may be preferably rounded at their corners.

Moreover, small circles may be formed at the ends of the linear cut lines 32 and the auxiliary traverse cut lines 34 so as to prevent the head holding portions 30 from being torn when the head holding portions 30 are pressed against the head.

In order to prevent the sign part 10 from being excessively bent over, a restriction means 40 may be attached to the sign part 10 and the remaining portion of the plate P, with one end of the restriction means 40 being fixed to the bottom surface of the sign part 10 and the other end of the restriction means 40 being fixed to the bottom surface of the remaining portion of the plate P. The restriction means 40 preferably has a length as long as the restriction means 40 lies tightly on the head when the sign part 10 stands erect as the head is inserted into the head insertion hole 10*a*. Further, the restriction means 40 may be a band and a net, the net being worn on the upper half of the head.

A plurality of portions for connecting the sign part 10 with the remaining portion of the plate P are preferably formed in the circumferential line 14, thereby preventing the sign part 10 from standing at an undesirable angle.

The plate P may be made of various materials, but be preferably made of paper that has sufficient strength capable of allowing the paper to keep its plane and permits the headgear to be manufactured at a low cost. Although the plate P is illustrated to have an arch-shape, the plate P may have various shapes according to its purpose.

The use of the headgear is described in the following.

The headgear may be initially used as a cheering card. That is, since the sign part 10 is connected to the remaining portion of the plate P through the connecting portions 20 so that the headgear initially forms a plate, a participant or spectator who has the headgear may conveniently use the headgear as a cheering card.

When the participants or spectators does not participate in cheering, the sign part may be capable of standing erect if the connecting portions 20 are cut. In this state, if the head is inserted into the head insertion hole 10*a*, the sign part 10 is rotated around the folding line 12 and stands erect, and the head holding portions 30 stand erect and press against the head, so that the headgear is worn by a participant or a spectator.

In such a case, since the sign part 10 is restricted to stand vertically by the restriction means 40, the items appearing in the sign part 10 are shown to the front, so that the headgear may serve to not only perform a display function with regard to an advertisements function, a public relations function and a cheering function, but also maintain the unity of participants or spectators. Of course, in this case, the headgear serves to obstruct the rays of the sun, also.

Incidentally, the restriction means regulates the insertion depth of the head. If the restriction means 40 is fixed to pass across the head insertion hole 10*a*, the restriction means lies on the user's head when a user wears the headgear. As a result, the insertion depth of the head may be regulated by adjusting the length of the restriction means 40.

As described above, the present invention provides head gear for advertisements, public relations and cheering as well as shading, which not only obstructs the rays of the sun and serves as a display when the sign part stands erect, but also is used as a cheering card and a publicity plate when the sign part is not erected.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. Headgear for advertisements, public relations and cheering as well as shading, wherein a head insertion hole and a sign part are defined on a center portion of a plate by a circumferential cut line and a front folding line; and a plurality of linear cut lines, which are extended radially outwardly from the circumferential cut line, and are formed on a portion of the plate outside of the sign part while being spaced apart from each other, thereby forming head holding portions between every two linear cut lines.

2. The headgear according to claim 1, wherein auxiliary traverse cut lines are formed to pass through ends of the alternate linear cut lines, respectively, so that a resilient action of the head holding is easily performed.

3. The headgear according to claim 1, further comprising a restriction means that is attached to said sign part and a remaining portion of the plate, with a first end of the restriction means being fixed to a bottom surface of the sign part and a second end of the restriction means being fixed to a bottom surface of the remaining portion of the plate, so as to prevent the sign part from being bent over excessively.

4. The headgear according to claim 3, wherein said restriction means is a relatively wide net.

5. The headgear according to claim 1, wherein said sign part and a remaining portion of a plate are connected by a plurality of connecting portions so as to prevent the sign part from standing at an undesirable angle.

* * * * *